United States Patent [19]
Scolton

[11] Patent Number: 5,877,428
[45] Date of Patent: Mar. 2, 1999

[54] APPARATUS AND METHOD FOR MEASURING ELASTOMERIC PROPERTIES OF A SPECIMEN DURING A TEST PROCEDURE

[75] Inventor: Chris J. Scolton, La Rose, Ill.

[73] Assignee: Caterpillar Inc., Peoria, Ill.

[21] Appl. No.: 865,263

[22] Filed: May 29, 1997

[51] Int. Cl.⁶ .................................................. G01N 11/00
[52] U.S. Cl. ............................................. 73/822; 73/823
[58] Field of Search ........................... 73/790, 818, 821, 73/822, 823, 862.621, 862.636, 862.637

[56] References Cited

U.S. PATENT DOCUMENTS

| | | | |
|---|---|---|---|
| 2,628,496 | 2/1953 | Wick | 73/818 |
| 3,252,321 | 5/1966 | Frann | 73/818 |
| 3,550,441 | 12/1970 | Dickinson | 73/818 |
| 3,754,438 | 8/1973 | Matson | 73/141 A |
| 4,998,825 | 3/1991 | Hublikar et al. | 374/50 |
| 5,119,681 | 6/1992 | Miszczak | 73/788 |
| 5,383,986 | 1/1995 | Cho | 148/697 |
| 5,392,005 | 2/1995 | Bortolini et al. | 331/44 |
| 5,458,002 | 10/1995 | Askea et al. | 73/789 |
| 5,471,877 | 12/1995 | Brown | 73/571 |
| 5,471,885 | 12/1995 | Wagner | 73/862.041 |
| 5,599,408 | 2/1997 | Fujita et al. | 148/607 |

OTHER PUBLICATIONS

Catalog listing of "Precision Pancake Thin Load Cells", Sensotec, Incorporated, pp. LO–2 and LO–3.
Jerome Pala et al., "Retention of Sealing Force by Elastomeric Gaskets", *SAE Technical Papers*, 1987, pp. 1–16.
Mark V. Bower, "Viscoelastic Analysis of Seals for Extended Service Life", University of Alabama, 1993, pp. III–1–III–4.
Mark A. Belchuk, "Stress Relaxation as Used in Underhood Component Design Verification", Joh Rubber Inc. No date.
R.G.Clinton et al., "Long Term Compression Effects on Elastomeric O–Ring Behavior", National Aeronautics and Space Administration, 1990, pp. 53–61.
William M. Bunting et al., "Compression Stress Relaxation I: An Important Test for Evaluation of Sealant Materials", GE Silicones, pp. 35–43. No date.
William M. Bunting et al., "Compression Stress Relaxation III: Provides Improved New Product Direction", GE Silicones, pp. 1–6. no date.
William M. Bunting et al., "Compression Stress Relaxation: An Improvement Over Traditional Tests for the Evaluation of Sealant Materials", GE Silicones, pp. 1–12, Tables I–VI, Figures 1–6. no date.
Abraham Pannikottu et al., "Predicting Elastomeric Gasket Performance", *Rubber & Plastics News*, Nov. 18, 1996, pp. 44–45.
"Rubber, Vulcanized or Thermoplastic—Determination of Stress Relaxation in Compression at Ambient and at Elevated Temperatures", International Organization for Standardization, ISO 3384, 1992.

*Primary Examiner*—Max H. Noori
*Attorney, Agent, or Firm*—Alan J. Hickman; Paul J. Maginot

[57] ABSTRACT

An apparatus for measuring elastomeric properties of a specimen during a test procedure includes a first compression member. The apparatus also includes a second compression member. Moreover, the apparatus includes a load cell having a body and a movable probe. The body is fixed in relation to the first compression member. The apparatus also includes a load transferring member positioned in contact with the probe. The specimen is interposed between the load transferring member and the second compression member. The apparatus also includes a bolt which contacts both the first compression member and the second compression member so as to maintain a constant distance therebetween during the test procedure. A method for measuring elastomeric properties of a specimen during a test procedure is also disclosed.

13 Claims, 6 Drawing Sheets

APPARATUS AND METHOD FOR MEASURING ELASTOMERIC PROPERTIES OF A SPECIMEN DURING A TEST PROCEDURE

BACKGROUND OF THE INVENTION

The present invention relates generally to a measuring device, and more particularly to an apparatus and method for measuring elastomeric properties of a specimen during a test procedure.

Sealing members such as O-rings or gaskets are commonly made of elastomeric materials. Elastomeric materials are advantageous in that the O-ring made therewith is generally conformable, free of porosity, and relatively resilient thereby creating a relatively impermeable seal when positioned between two flat plates or flanges.

Over a period of time, the effectiveness of the seal created by an elastomeric O-ring may diminish. In particular, the O-ring is initially positioned between two plates or flanges, such as a mating flange of a water pump and a corresponding mating flange of a fluid inlet line, thereby compressing the O-ring when the two plates are secured to one another. The compressed O-ring exerts a force back against the two plates. Such a force is commonly and hereinafter referred to as a "sealing force" of the O-ring. Over a period of time, the sealing force of the O-ring relaxes or otherwise decreases thereby potentially causing a leak to occur between the two mating flanges in the case of the water pump and fluid inlet line.

A number of variables affect the rate at which the sealing force of the O-ring relaxes. For example, the type of elastomeric material which is used to make the O-ring affects the rate at which the sealing force of the O-ring relaxes. In addition, exposing the O-ring to an aging fluid such as air, water, gasoline, brake fluid, or engine coolant also affects the rate at which the sealing force of the O-ring relaxes. Moreover, exposing the O-ring to environmental conditions such as varying temperatures affects the rate at which the sealing force of the O-ring relaxes.

Therefore, a number of load measuring apparatuses have heretofore been developed to measure the rate at which the sealing forces of an elastomeric material relax. Such load measuring apparatuses, often referred to as relaxometers, generally include a test fixture in which an elastomeric test specimen is clamped. Such load measuring apparatuses further include a measuring instrument which is used to measure the sealing forces being exerted by the test specimen. The test fixture may be removed from the measuring instrument, and thereafter subjected to a variety of aging conditions such as heated fluid baths and ovens. After which, the test fixture is reinstalled in the measuring instrument in order to perform subsequent measurements.

There are a number of drawbacks associated with the use of the aforementioned load measuring apparatuses. For example, it is undesirable to repeatedly remove the test fixture from the measuring instrument. This is true since excessive handling of the test fixture may cause the test specimen to be jarred or otherwise moved, thereby potentially causing erroneous or otherwise invalid test data.

Moreover, the sealing force of the test specimen may only be measured at predetermined intervals during a test procedure. For example, the sealing force of the test specimen may be measured prior to placing the test fixture in an aging fluid bath. Thereafter, the test fixture may be removed from the aging fluid bath at predetermined intervals, such as every fifty hours, and placed in the measuring instrument in order to measure the sealing force at that particular interval. Hence, after 200 hours, relaxation of the sealing forces may be shown as the slope of a line with only five data points. Although the frequency of the intervals at which the test fixture is removed from the aging fluid bath may be increased, such frequency is for practical reasons limited by the amount of time necessary for an operator of the load measuring apparatus to (1) remove the test fixture from the aging fluid bath, (2) prepare the test fixture for measuring (e.g. clean the test fixture), (3) heat the test fixture to a testing temperature, (4) install the test fixture in the measurement instrument, (5) obtain the measurement, and (6) replace the test fixture in the aging fluid bath.

In addition, load measuring apparatuses which have heretofore been designed are relatively large thereby requiring a relatively large amount of space in a lab. Moreover, load measuring apparatuses which have heretofore been designed are relatively mechanically complex and financially expensive.

What is needed therefore is an apparatus and method for measuring elastomeric properties of a specimen during a test procedure which overcomes one or more of the above-mentioned drawbacks.

SUMMARY OF THE INVENTION

In accordance with a first embodiment of the present invention, there is provided an apparatus for measuring elastomeric properties of a specimen during a test procedure. The apparatus includes a first compression member. The apparatus further includes a second compression member spaced apart from the first compression member. The apparatus also includes a load cell having a body and a movable probe. The body is fixed in relation to the first compression member. The specimen is interposed between the movable probe and the second compression member. Moreover, the apparatus includes a connecting mechanism which spaces the first compression member apart from the second compression member by a constant distance during the test procedure.

In accordance with a second embodiment of the present invention, there is provided an apparatus for measuring elastomeric properties of a specimen during a test procedure. The apparatus includes a first compression member. The apparatus also includes a second compression member. Moreover, the apparatus includes a load cell having a body and a movable probe. The body is fixed in relation to the first compression member. The apparatus also includes a load transferring member positioned in contact with the probe. The specimen is interposed between the load transferring member and the second compression member. The apparatus also includes a bolt which contacts both the first compression member and the second compression member so as to maintain a constant distance therebetween during the test procedure.

In accordance with a third embodiment of the present invention, there is provided a method of measuring elastomeric properties of a specimen during a test procedure. The method involves the step of providing a load measuring assembly. The load measuring assembly has a first compression member. The load measuring assembly also includes a second compression member spaced apart from the first compression member. Moreover, the load measuring assembly includes a load cell having a body and a movable probe, the body being fixed in relation to the first compression member, and the specimen being interposed between the movable probe and the second compression member. The load measuring assembly also has a connecting mechanism which spaces the first compression member apart from the second compression member by a constant distance during the test procedure. The method also includes the step of exposing the load measuring assembly to an aging fluid. Moreover, the method includes the step of generating test data based on elastomeric properties of the specimen with the load cell during the exposing step.

BEST MODE FOR CARRYING OUT THE INVENTION

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 1:
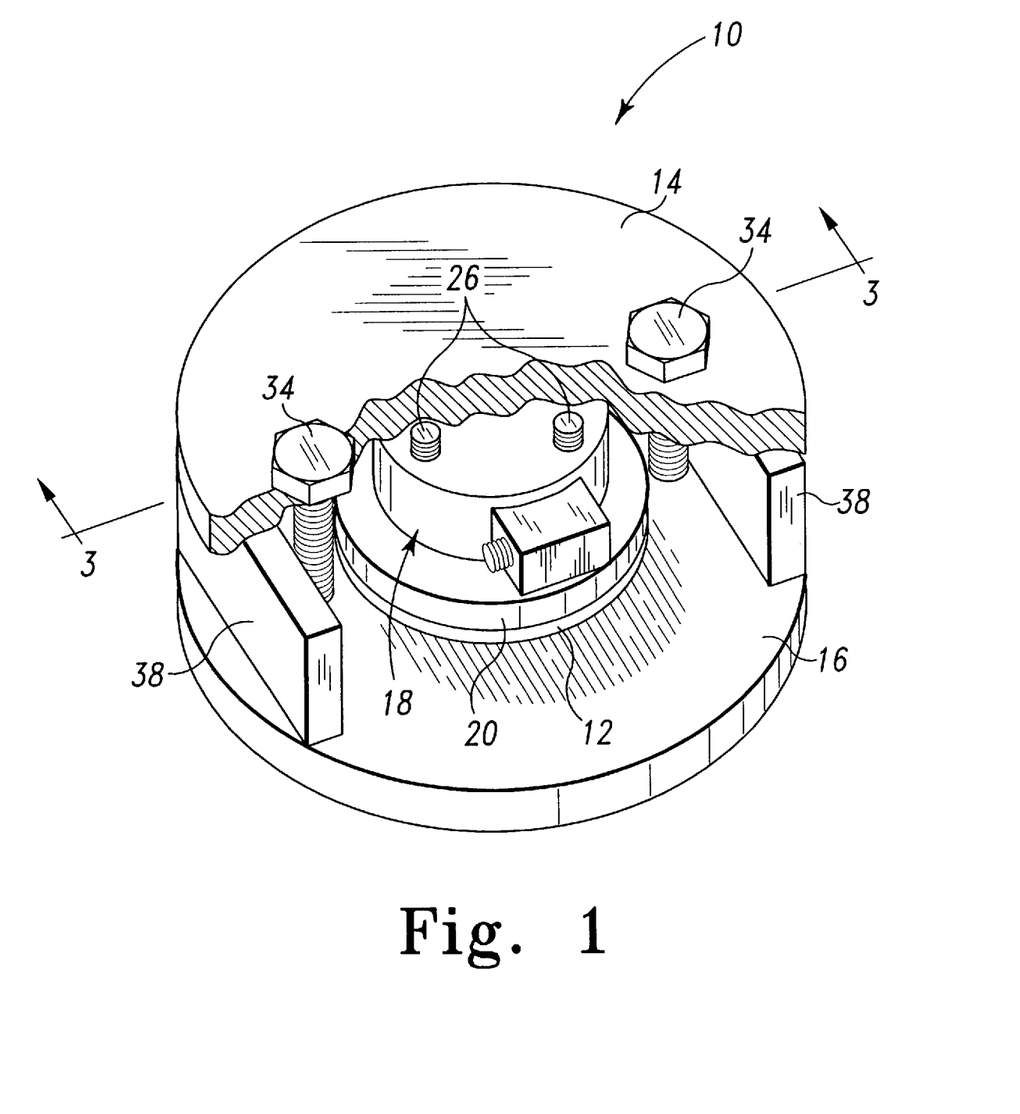
FIG. 1 is a fragmentary perspective view of a load measuring assembly which incorporates the features of the present invention therein.
Figure 2:
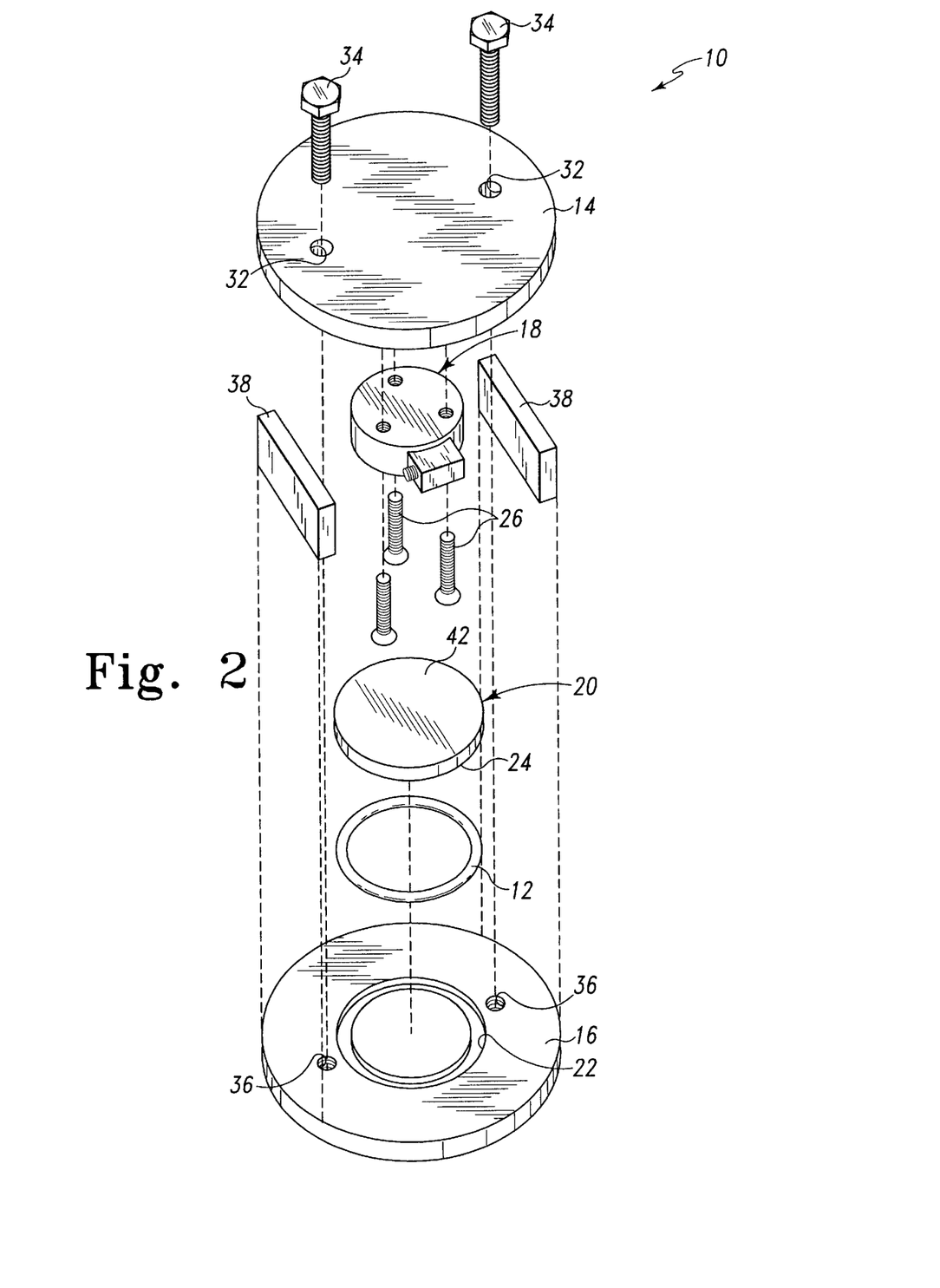
FIG. 2 is a reduced exploded perspective view of the load measuring assembly of FIG. 1.
Figure 3:
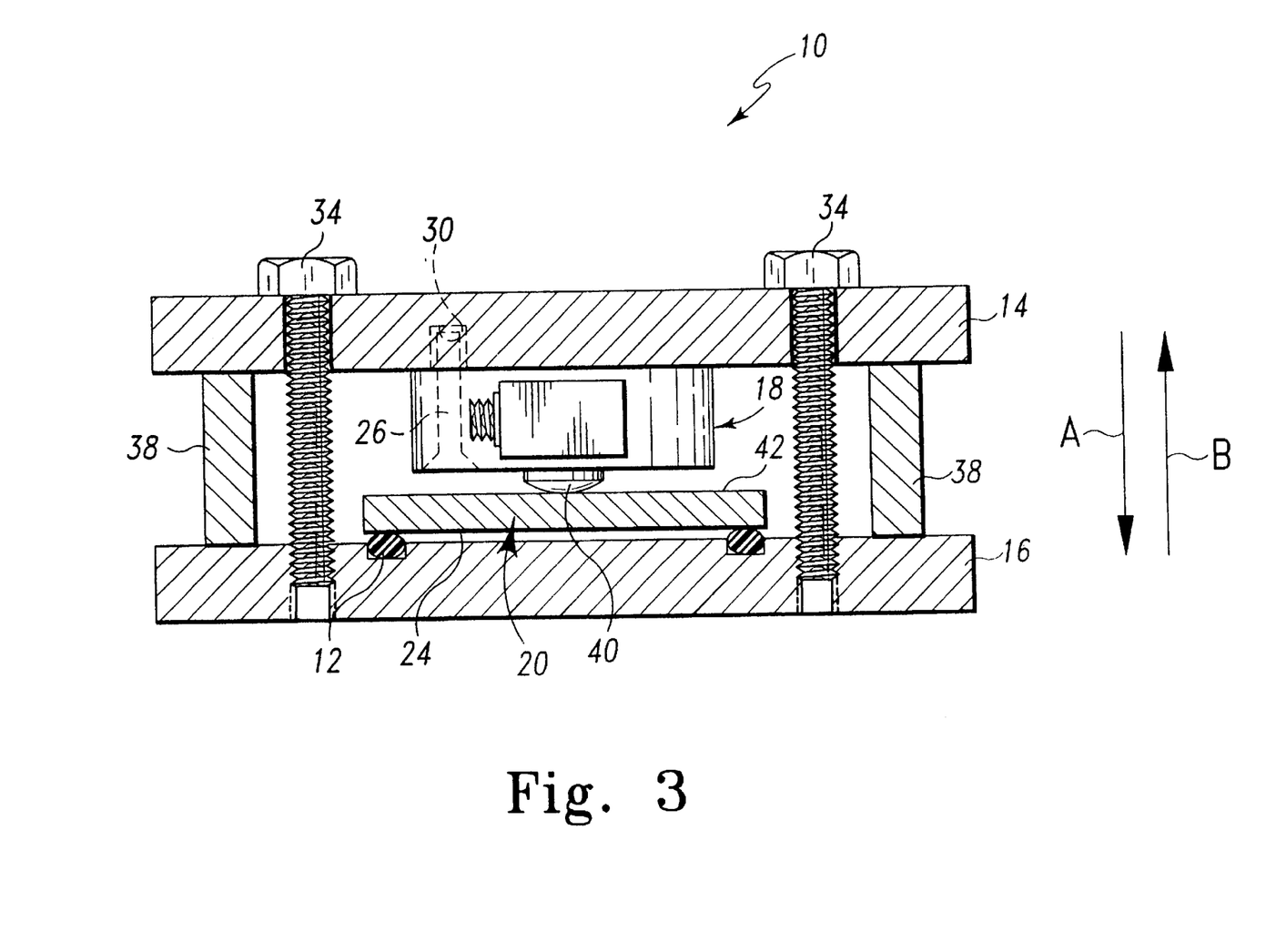
FIG. 3 is a cross sectional view taken along the line 3—3 of FIG. 1, as viewed in the direction of the arrows (Note: the load cell 18 and the compressing bolts 34 are not shown in cross section for clarity of description)

Referring now to FIGS. 1–3, there is shown a load measuring assembly 10. The load measuring assembly 10 is used to measure a sealing force or load being exerted by a test specimen such as an O-ring 12. The load measuring assembly 10 includes an upper compression member 14, a lower compression member 16, a load cell 18, and a load transferring member 20. As shown in FIG. 2, the compression members 14, 16 are preferably flat, circular-shaped plates.

The O-ring 12 is made of an elastomeric material such as rubber, and may be used for creating a seal between components of a diesel engine (not shown). For example, the O-ring 12 may be used to seal a mating flange of a water pump (not shown) to a corresponding mating flange of a fluid inlet line (not shown).

Figure 4:
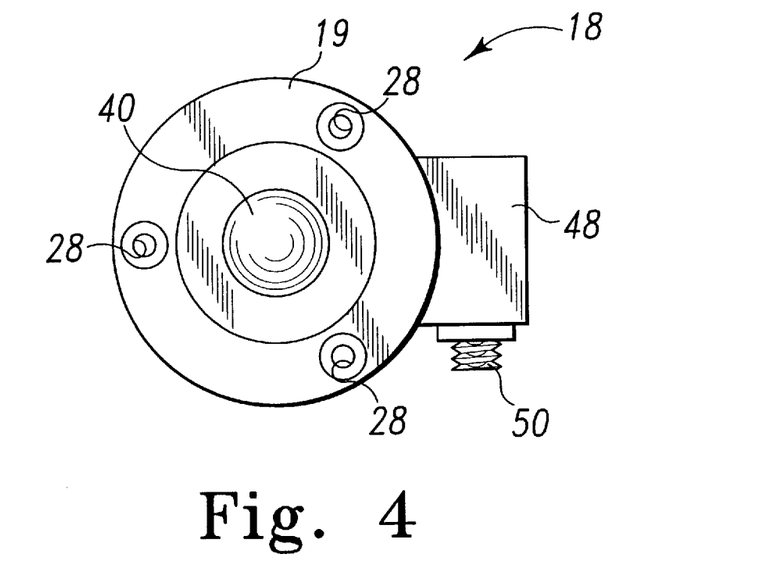
FIG. 4 is a reduced top elevational view of the load cell of the load measuring assembly of FIG. 1.
Figure 6:
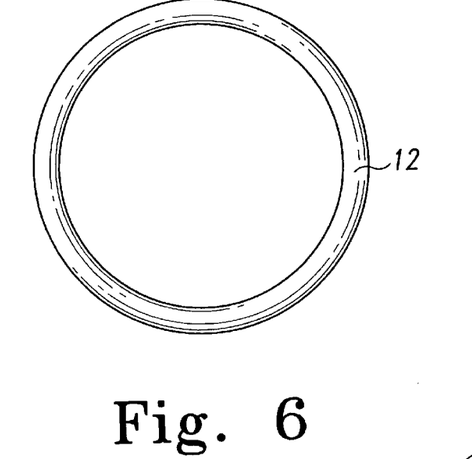
FIG. 6 is an enlarged top elevational view of an O-ring whose characteristics may be measured by the load measuring assembly of FIG. 1.
Figure 7:
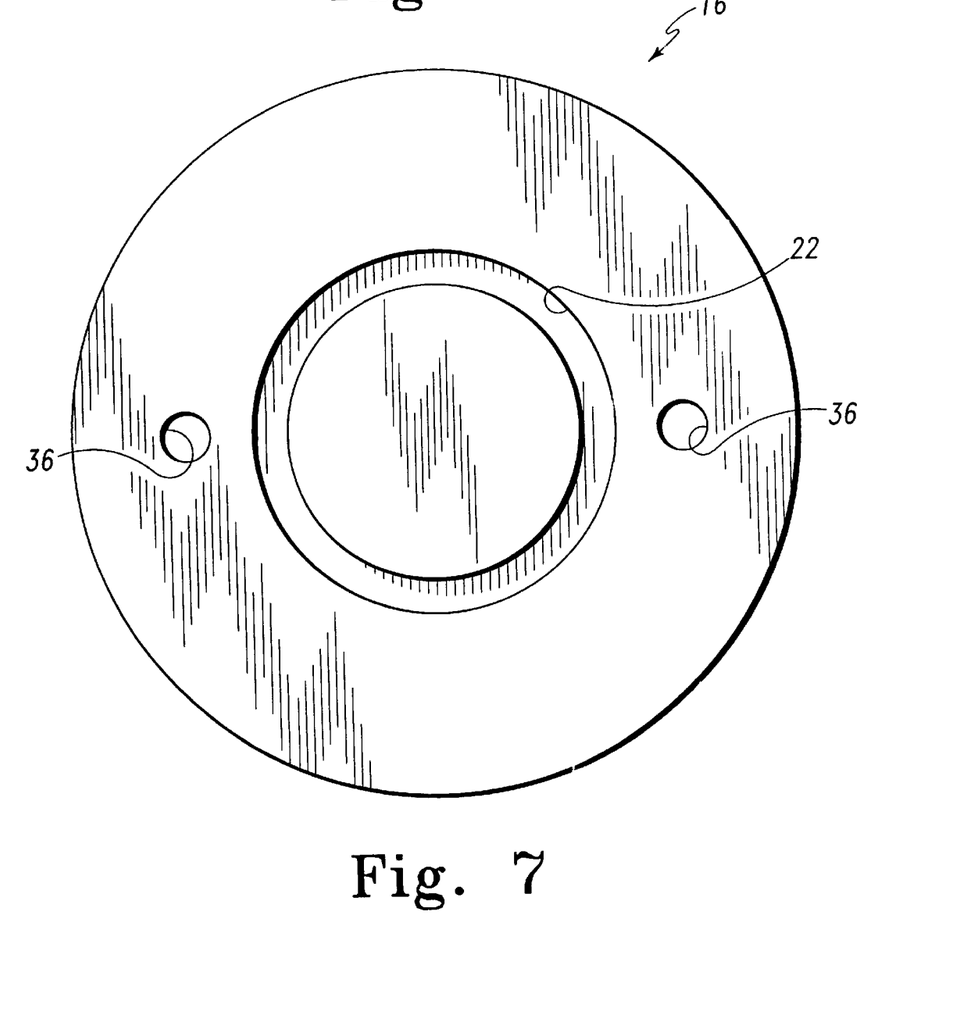
FIG. 7 is an enlarged top elevational view of the lower compression member of the load measuring assembly of FIG. 1.

The O-ring 12 has a substantially circular shape as shown in FIG. 6, and is positionable in a ring groove 22 (see FIG. 7) defined in the lower compression member 16. The O-ring 12 is compressed within the ring groove 22 by a compressing force generated by the load measuring assembly 10 which is transmitted through the upper compression member 14. In particular, a bottom surface 24 of the load transferring member 20 contacts the O-ring 12 as shown in FIG. 3. The load cell 18 is secured to the upper compression member 14 via a number of mounting bolts 26. More specifically, a body 19 of the load cell 18 has a number of apertures 28 (see FIG. 4) defined therein. The mounting bolts 26 are received through the apertures 28, and thereafter threadingly engaged into a number of mounting holes 30 (see FIG. 3) defined in the upper compression member 14 thereby securing the body 19 of the load cell 18 to the upper compression member 14.

The upper compression member 14 further has a number of compressing holes 32 defined therein. The compressing holes 32 are provided to receive a number of compressing bolts 34 therethrough. Thereafter, the compressing bolts 34 are threadingly engaged in a number of compressing holes 36 defined in the lower compression member 16. It should therefore be appreciated that the O-ring 12 may be compressed by adjusting the compressing bolts 34. In particular, if the compressing bolts 34 are tightened, the O-ring 12 will be further compressed, whereas if the compressing bolts 34 are loosened, the compression on the O-ring 12 will be lessened.

In order to provide a compression of an initial, predetermined magnitude on the O-ring 12, the load measuring assembly 10 further includes a number of shims 38. As shown in FIG. 3, the shims 38 are interposed between the upper compression member 14 and the lower compression member 16. The height of the shims 38 is configured such that the O-ring 12 is compressed a predetermined magnitude when the compressing bolts 34 are installed. More specifically, the shims 38 prevent the upper compression member 14 from being urged in the general direction of arrow A of FIG. 3 beyond a predetermined limit thereby limiting the amount of compressing force which is exerted on the O-ring 12, which in turn compresses the O-ring 12 to a predetermined magnitude. For example, the height of the shims 38 may be configured such that the O-ring 12 is compressed 25% when the compressing bolts 34 are installed.

When compressed, the O-ring 12 exerts the sealing force onto the load transferring member 20. The magnitude of the sealing force is measured by the load cell 18. In particular, the load cell 18 includes a movable probe 40 extending outwardly from the body 19 of the load cell 18. The movable probe 40 contacts a top surface 42 of the load transferring member 20. Therefore, as the sealing force of the O-ring 12 urges the load transferring member 20 in the general direction of arrow B of FIG. 3, the movable probe 40 of the load cell 18 detects the magnitude of the sealing force being exerted by the O-ring 12. Thereafter, the load cell 18 converts the magnitude of the detected sealing force into an electrical signal which is sent to a processing unit 44 via a signal line 46 (see FIG. 8).

The load cell 18 is a low profile, "pancake" type load cell. The load cell 18 may detect loads of various magnitudes and ranges. For example, the load cell 18 may detect loads ranging from 5 to 400,000 pounds. One type of load cell 18 which is suitable for use in the present invention is a Sensotec Load Cell Model 43 which is commercially available from Sensotec, Incorporated of Columbus, Ohio.

Moreover, the body 19 of the load cell 18 includes a terminal block 48. The terminal block 48 includes a threaded electrical coupling 50. The signal line 46 (see FIG. 8) has a threaded coupling (not shown) at a first end thereof which mates to the threaded coupling 50. Hence, the load cell 18 is electrically coupled to the processing unit 44 when the first end of the signal line 46 is coupled to the threaded coupling 50, and a second end of the signal line 46 is coupled to the processing unit 44. The signal line 46 is preferably made of materials which can withstand various environmental testing conditions, such as the presence of relatively high or low temperatures and chemical aging fluids. For example, the signal line 46 may include one or more Teflon cables which are commercially available from Sensotec, Incorporated.

The processing unit 44 (see FIG. 8) may be any known processing unit which is capable of receiving data from the load cell 18 and storing such data in an electronic file for subsequent processing thereof. Moreover, the processing unit 44 may include an analog interface circuit (not shown) which converts the output signals from the load cell 18 into a signal which is suitable for presentation to an input of a microprocessor (not shown) of the processing unit 44. In particular, the analog interface circuit converts the output signals on the signal line 46 into amplified analog voltages. It should be appreciated that the magnitude of the analog voltage on the signal line 46 is indicative of the magnitude of the sealing force being exerted by the O-ring 12 onto the load transferring member 20 (see FIG. 3). An analog-to-digital (A/D) converter (not shown) then converts the analog voltages into a digital value for use by the microprocessor. It should be appreciated that the processing unit 44 may, for example, be a known personal computer (PC).

Figure 8:
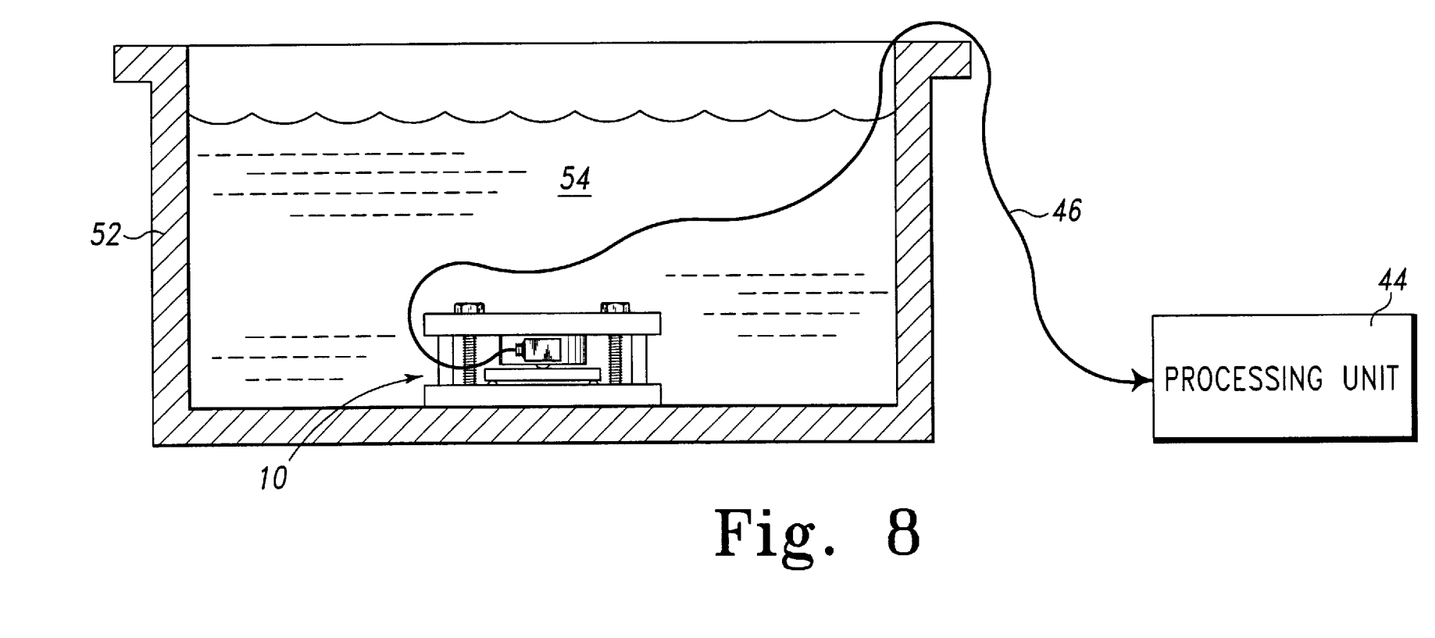
FIG. 8 is a view showing the load measuring assembly of FIG. 1 submersed in the fluid tank, with the load cell shown schematically coupled to the processing unit.

The processing unit 44 may be used to collect "real-time" data during a given test procedure during which the load measuring assembly 10 is exposed to various aging fluids. For example, the load measuring assembly 10 may be submersed in a fluid tank 52 containing a liquid aging fluid 54, such as engine coolant or diesel fuel as shown in FIG. 8. While positioned in the fluid tank 52, the load cell 18 generates a continuous stream of test data which is transferred to the processing unit 44. Hence, test data may be collected during the entire test procedure. The liquid aging fluid 54 may be heated to relatively high temperatures or chilled to relatively low temperatures depending on the desired environmental parameters of a given test procedure.

Alternatively, the load measuring assembly 10 may be positioned in an oven (not shown) or the like and subjected to relatively high temperatures in the presence of a gaseous aging fluid such as air. While positioned in the oven, the load cell 18 generates a substantially continuous stream of test data which is transferred to the processing unit 44. Hence, test data may be collected during the entire test procedure.

As discussed above, the load measuring assembly 10 is exposed to environmental conditions which fluctuate between relatively high temperatures and relatively low temperatures during a given test procedure. Hence, the various components associated with the load measuring assembly 10 are preferably made from an alloy which is relatively resistant to expansion and contraction during such temperature fluctuations. In particular, the compression members 14 and 16, the body 19 and the movable probe 40 of the load cell 18, the load transferring member 20, the bolts 26 and 34, and the shims 38 are preferably made of an iron-nickel-carbon alloy. One such iron-nickelcarbon alloy suitable for use in the present invention is Invar.

Industrial Applicability

In operation, the O-ring 12 is first positioned in the ring groove 22 (see FIG. 7) of the bottom compression member 16. Thereafter, the load transferring member 20 is positioned on top of the O-ring 12. The shims 38 may then be positioned on the lower compression member 16.

Once the shims 38 are in place, the upper compression member 14, with the load cell 18 secured thereto via the mounting bolts 26, may then be lowered into contact with the shims 38. The compressing bolts 34 are then advanced through the compressing holes 32 of the upper compression member 14. Thereafter, the compressing bolts 34 threadingly engage the compressing holes 36 of the lower compressing member 16. The compressing bolts 34 are tightened until the upper compression member 14 is urged into contact with the shims 38 thereby compressing the O-ring 12 to a predetermined magnitude such as 25%.

Figure 5:
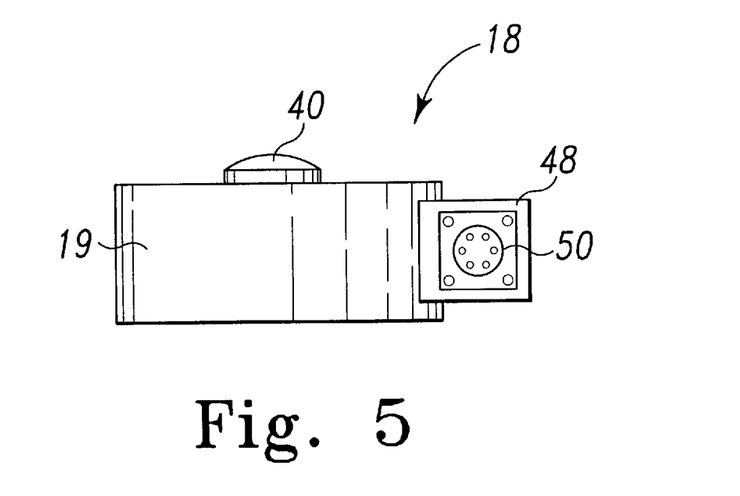
FIG. 5 is a side elevational view of the load cell of FIG. 4.

Once the load measuring assembly 10 has been assembled in the manner previously described, the load cell 18 may begin to measure elastomeric properties of the O-ring 12, such as the magnitude of the sealing force generated thereby. More specifically, the first end of the signal line 46 (see FIG. 8) may be connected to the threaded electrical coupling 50 (see FIGS. 4–5) of the load cell 18, whereas the second end of the signal line 46 may be connected to the processing unit 44 (see FIG. 8). Thereafter, the movable probe 40 of the load cell 18 detects the magnitude of the sealing force that is exerted on the load transferring member 20 by the O-ring 12. Once the magnitude of the sealing force is detected, the load cell 18 generates test data in the form of a stream of electrical output signals which is transferred to the processing unit 44 via the signal line 46. Once transferred to the processing unit 44, the test data may be stored in the memory device thereof, such as the hard drive, for subsequent processing and analysis.

If a particular test procedure so requires, the load measuring assembly 10 may be positioned in the fluid tank 52 thereby being submersed in the liquid aging fluid 54. The load measuring assembly 10 may remain in the fluid tank 52 for a predetermined period of time, as required by a particular test procedure. The load cell 18 will continue to generate and transfer a stream of test data during the period of time in which the load measuring assembly is 10 positioned in the fluid tank 52. Moreover, if a particular test procedure so requires, the load measuring assembly 10 may be positioned in the oven (not shown) and subjected to relatively high temperatures in the presence of a gaseous aging fluid such as air. Once positioned in the oven, the load cell 18 will continue to generate and transfer a stream of test data during the period of time in which the load measuring assembly 10 is positioned in the oven.

As described above, the load measuring assembly 10 enables the collection of real-time test data while the specimen (i.e. the O-ring 12) is being exposed to an aging fluid (i.e. a liquid aging fluid such as cooling fluid or diesel fuel, or a gaseous aging fluid such as air). The collection of test data in such a manner provides a larger number of data points over a given period of time relative to load measuring apparatuses which have heretofore been designed. Moreover, the collection of data in such a manner eliminates the need to remove the specimen from the aging fluid for measuring purposes during the test procedure. Therefore, the number of occasions in which the specimen may be disadvantageously jarred or otherwise moved during the test procedure is reduced or eliminated.

While the invention has been illustrated and described in detail in the drawings and foregoing description, such illustration and description is to be considered as exemplary and not restrictive in character, it being understood that only the preferred embodiment has been shown and described and that all changes and modifications that come within the spirit of the invention are desired to be protected.

It should be appreciated that although the specimen is described herein as the O-ring 12, the load measuring assembly 12 may be used to measure elastomeric properties of any type of elastomeric material. For example, the specimen may be a silicone rubber gasket or a nitrile rubber washer.

It should also be appreciated that although the load measuring assembly 10 is described herein as being completely submersed in the liquid aging fluid 54 when positioned in the fluid tank 52, the load measuring assembly 10 may be only partially submersed in the aging fluid 54. For example, the load measuring assembly 10 may be positioned in the fluid tank 52 such that only the lower compression member 16 and the O-ring 12 are submersed in the aging fluid 54. In addition, the load measuring assembly 10 may be positioned in the fluid tank 52 such that only the lower compression member 16 and a portion of the O-ring 12 are submersed in the aging fluid 54.

what is claimed is:

1. An apparatus for measuring stress relaxation properties of an elastomeric specimen during a test procedure, comprising:

a first compression member;

a second compression member spaced apart from said first compression member;

a load cell having a body, a movable probe, and being adapted to deliver data in real time during the test procedure, said body being fixedly connected to said first compression member and said specimen being interposed between said movable probe and said second compression member; and a connecting mechanism connecting said first compression member to said second compression member and maintaining the first compression member from moving closer to said second compression member than a fixed predetermined spaced distance during said test procedure, said connecting mechanism includes a shim which is positioned between said first compression member and said second compression member.

2. An apparatus for measuring stress relaxation properties of an elastomeric specimen during a test procedure, comprising:

a first compression member having a first aperature defined therein;

a second compression member having a second aperature defined therein and spaced apart from said first compression member;

a load cell having a body, a movable probe, and being adapted to deliver data in real time during the test procedure, said body being fixedly connected to said first compression member and said specimen being interposed between said movable probe and said second compression member; and a connecting mechanism connecting said first compression member to said second compression and maintaining the first compression member at a fixed predetermined spaced distance from said second compression member during said test procedure, said connecting mechanism includes a bolt extending through said first aperture and into screwthreadable engagement with said second aperture so as to connect.

3. An apparatus for measuring stress relaxation properties of an elastomeric specimen during a test procedure, comprising:

a first compression member;

a second compression member spaced apart from said first compression member;

a load cell having a body, a movable probe, and being adapted to deliver data in real time during the test procedure, said body being fixedly connected to said first compression member and said specimen being interposed between said movable probe and said second compression member; and a connecting mechanism having a plurality of spaced apart shims disposed between and contactable with the first and second compression members, said plurality of shims defining a fixed predetermined spaced distance between said first and second compression members, said connecting mechanism connecting said first compression member to said second compression member and maintaining the first compression member at said fixed predetermined spaced distance from said second compression member during said test procedure.

4. The apparatus of claim 1, including a load transferring member positioned in contact with said probe, said specimen being interposed between said load transferring member and said second compression member.

5. The apparatus of claim 4, wherein said load transferring member being interposed between said probe of said load cell and said specimen.

6. The apparatus of claim 4, wherein said second compression member having a groove defined therein, said specimen being positionable in said groove, and said specimen being located between said second compression member and said load transferring member when said specimen is positioned in said groove.

7. The apparatus of claim 1, wherein said first compression member and said second compression member are each a plate.

8. The apparatus of claim 1, wherein said specimen is an O-ring.

9. A method of measuring stress relaxation properties of an elastomeric specimen during a test procedure, comprising the steps of:

providing a load measuring assembly having a first compression member, a second compression member spaced apart from the first compression member, a load cell having a body, a movable probe and being adapted to deliver data in real time during the test procedure, the body being fixedly connected to the first compression member and the specimen being interposed between the movable probe and the second compression member, and a connecting mechanism connecting the first compression member to the second compression member and maintaining the first compression member at a fixed predetermined spaced distance from said second compression member during the test procedure;

exposing the load measuring assembly to an aging fluid during said testing procedure; and generating test data based on the stress relaxation properties of the specimen with the load cell in real time during the exposing step.

10. The method of claim 9, wherein the exposing step includes the step of exposing the load measuring assembly to a liquid aging fluid bath.

11. The method of claim 10, wherein the step of exposing the load measuring assembly to the liquid aging fluid bath includes the step of submersing the load measuring assembly in the liquid aging fluid bath.

12. The method of claim 9, wherein the exposing step includes the step of exposing the load measuring assembly to a gaseous aging fluid.

13. The method of claim 9, further comprising the step of transferring test data in real time from the load cell to a processing unit during the exposing step.

* * * * *